(12) United States Patent
Sanjay-Gopal

(10) Patent No.: US 11,482,324 B2
(45) Date of Patent: *Oct. 25, 2022

(54) SYSTEMS AND METHODS FOR PERSONALIZED CARE MANAGEMENT

(71) Applicant: Sethumadavan Sanjay-Gopal, Viera, FL (US)

(72) Inventor: Sethumadavan Sanjay-Gopal, Viera, FL (US)

( * ) Notice: Subject to any disclaimer, the term of this patent is extended or adjusted under 35 U.S.C. 154(b) by 12 days.

This patent is subject to a terminal disclaimer.

(21) Appl. No.: 17/334,689

(22) Filed: May 29, 2021

(65) Prior Publication Data

US 2021/0287787 A1  Sep. 16, 2021

Related U.S. Application Data

(63) Continuation-in-part of application No. 16/581,787, filed on Sep. 25, 2019, now Pat. No. 11,139,073.

(51) Int. Cl.
| | |
|---|---|
| *G06F 21/31* | (2013.01) |
| *G06F 21/44* | (2013.01) |
| *G16H 40/20* | (2018.01) |
| *G16H 10/60* | (2018.01) |
| *G06F 16/23* | (2019.01) |
| *G16H 20/70* | (2018.01) |
| *G06K 7/14* | (2006.01) |
| *G16H 40/67* | (2018.01) |

(52) U.S. Cl.
CPC ......... *G16H 40/20* (2018.01); *G06F 16/2379* (2019.01); *G06K 7/1417* (2013.01); *G16H 10/60* (2018.01); *G16H 20/70* (2018.01); *G16H 40/67* (2018.01)

(58) Field of Classification Search
CPC ........ G16H 40/00; G16H 40/20; G16H 80/00; G16H 10/60; G06F 9/451; G06F 21/6281; G06F 21/31; G06F 9/4451; G10L 15/26
USPC ............. 713/155, 168, 183; 726/2, 4, 17, 27
See application file for complete search history.

(56) References Cited

U.S. PATENT DOCUMENTS

2017/0201850 A1* 7/2017 Raleigh .................. H04W 4/50
2018/0026984 A1* 1/2018 Maker .................. H04L 63/102
726/4

* cited by examiner

*Primary Examiner* — Izunna Okeke
(74) *Attorney, Agent, or Firm* — Rumit Ranjit Kanakia

(57) ABSTRACT

Disclosed are systems and methods for personalized care management. A plurality of user devices corresponding to a plurality of authorized caregivers are configured to provide input data to a processing module 1004. The input data is associated with an actionable item being performed for at least one care receiver, wherein the actionable item includes one of: a scheduled actionable item and a non-scheduled actionable item. The processing module 1004 receives, the at least one input data based on the scheduled actionable item and the non-scheduled actionable item. A profile of the at least one care receiver is updated based on the received at least one input data, and thereafter stored in a database 1010. The plurality of authorized caregivers is facilitated to access the stored updated profiles of the at least one care receiver for further analysis.

15 Claims, 10 Drawing Sheets

SYSTEMS AND METHODS FOR PERSONALIZED CARE MANAGEMENT

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

TECHNICAL FIELD

The disclosed subject matter relates to a system and method for personalized resident care management, more particularly the disclosed subject matter relates to a system and method to personalize information presentation to a user on a user device based on a specific assigned role to the user. Resident care management refers to managing the care for residents in an institutional setting such as an assisted living facility for the elderly. Care refers to both clinical (i.e. medical, behavioral) and non-clinical, i.e. social activities.

BACKGROUND

Resident care management solutions help care givers such as medical attendants, doctors, nurses, nursing assistants, spouses, family members, etc. These solutions help to maintain a smooth flow of information from one stop to the other. This helps in no break in information exchange. Also, since there are no breaks in information exchange hence, they make caregivers efficient.

However, the existing solutions are labor intensive. In most cases there is no electronic system and caregivers use manual processes. In cases where there are electronic systems, User has to complete a lot of formalities and has to process and fill information from various screens and interfaces. Such process makes task difficult and the objective of the smooth flow of information is not met. Further, there is also no automation within such solutions that helps other users to be informed when there is any modification or actionable item generated for them by one or more user(s).

Another drawback of such solution is that there is no customization of interface for different users. Also, there is no escalation procedure in case the actionable item is not fulfilled.

Therefore, there exists a need for an efficient care/resident management solution.

SUMMARY

This summary is provided to introduce concepts related to system and method for personalized resident care management concepts are further described in the detailed description. This summary is not intended to identify essential features of the claimed subject matter nor is it intended for use in determining or limiting the scope of the claimed subject matter.

In an implementation, a system for personalized care management is disclosed. The system may comprise a plurality of user devices corresponding to a plurality of users. Each user of the plurality of users have a specific assigned role. Further, each user device of the plurality of user devices provide an interactive user interface to its corresponding user. The system further includes a central controller that is connected to the plurality of user devices through a network. The central controller may comprise a processing module that may perform the steps comprising of receiving login credentials of the user through the user interface provided on the user device. The provided credentials are then cross checked, from a database. The database may store user IDs and corresponding credentials of the plurality of users. After this the processing module, retrieves a specific role assigned to the user and modifies information read/write layout based on the specific assigned role of the user.

In another implementation, a method for personalized care management is disclosed. The method may include the step of storing, in a database, profiles of a plurality of users. The method further includes registering, in the database, at least one corresponding user device for each of the plurality of users. Furthermore, the method may include step of receiving login credentials of the user through an interactive user interface that is provided on the user device. The method may further include, matching, by the processor, the login credentials received for authentication. The processor then, retrieves profile of the user post authentication and based on the profile of the user, information layout of the user interface presented to the user is modified.

Yet another embodiment of the present disclosure provides a communication system for providing personalized care management comprising: a plurality of user devices corresponding to a plurality of authorized caregivers, each user device providing an interactive user interface to: provide input data associated with an actionable item being performed for at least one care receiver, wherein the actionable item includes one of: a scheduled actionable item and a non-scheduled actionable item; a database for storing profiles of the authorized caregivers and profiles of the at least one care receiver; a central controller connected to the plurality of user devices through a communication network to facilitate the authorized caregivers to analyze the profiles of the at least one care receiver from a remote location; the central controller comprising a processing module configured to: receive, via the plurality of user devices, the at least one input data based on the scheduled actionable item; receive, via the plurality of user devices, the at least one input data based on the non-scheduled actionable item; update the profile of the at least one care receiver based on the received at least one input data; save the updated profile of the at least one care receiver in the database; and facilitate the authorized caregivers to further analyze the updated profile of the at least one care receiver.

In an aspect of the present disclosure, the profiles of the authorized caregivers are stored in different formats based on specific roles assigned to the authorized caregivers, and location of the plurality of user devices.

In an aspect of the present disclosure, the authorized caregivers include at least one of: a family member of the care receiver, an attendant for the care receiver, a nurse for the care receiver, a doctor for the care receiver, or a medicine administrator for the care receiver.

In an aspect of the present disclosure, the network is a wired or a wireless network, wherein the wireless network comprising at least one of: a mobile network, a satellite network, a Wi-Fi, or a Wireless Local Area Network (WLAN).

In an aspect of the present disclosure, the at least one input data includes a voice input, a text input, a video input, and a touch-based input.

In an aspect of the present disclosure, the actionable item includes medical care, psychological care, non-medical care, daily routine care, being provided to the at least one care-receiver by the plurality of authorized caregivers.

In an aspect of the present disclosure, the at least one input data based on the non-scheduled actionable item is inputted into the processing module through at least one QR Code scanner device.

In an aspect of the present disclosure, the at least one input data based on the non-scheduled actionable item is inputted into the processing module through at least one Beacon Transmitter.

In an aspect of the present disclosure, the non-scheduled actionable item includes one or more actions which are performed randomly for the care receiver.

In an aspect of the present disclosure, the scheduled actionable item includes one or more actions which are performed for the care receiver, according to a schedule prescribed by the corresponding authorized caregivers.

Yet another embodiment of the present disclosure provides a method for providing personalized care/resident management. The method comprises the steps of: configuring a plurality of user devices corresponding to a plurality of authorized caregivers, each user device providing an interactive user interface for: providing input data associated with an actionable item being performed for at least one care receiver, wherein the actionable item includes one of: a scheduled actionable item and a non-scheduled actionable item; configuring a database for storing profiles of the authorized caregivers and profiles of the at least one care receiver; configuring a central controller connected to the plurality of user devices through a communication network for facilitating the authorized caregivers to analyze the profiles of the at least one care receiver from a remote location; configuring a processing module for: receiving, via the plurality of user devices, the at least one input data based on the scheduled actionable item; receiving, via the plurality of user devices, the at least one input data based on the non-scheduled actionable item; updating the profile of the at least one care receiver based on the received at least one input data; saving the updated profile of the at least one care receiver in the database; and facilitating the authorized caregivers to further analyze the updated profile of the at least one care receiver.

Other and further aspects and features of the disclosure will be evident from reading the following detailed description of the embodiments, which are intended to illustrate, not limit, the present disclosure.

BRIEF DESCRIPTION OF THE DRAWINGS

The illustrated embodiments of the subject matter will be best understood by reference to the drawings, wherein like parts are designated by like numerals throughout. The following description is intended only by way of example, and simply illustrates certain selected embodiments of devices, systems, and processes that are consistent with the subject matter as claimed herein.

DETAILED DESCRIPTION

A few inventive aspects of the disclosed embodiments are explained in detail below with reference to the various figures. Embodiments are described to illustrate the disclosed subject matter, not to limit its scope, which is defined by the claims. Those of ordinary skill in the art will recognize a number of equivalent variations of the various features provided in the description that follows.

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures or characteristics may be combined in any suitable manner in one or more embodiments.

Figure 1:
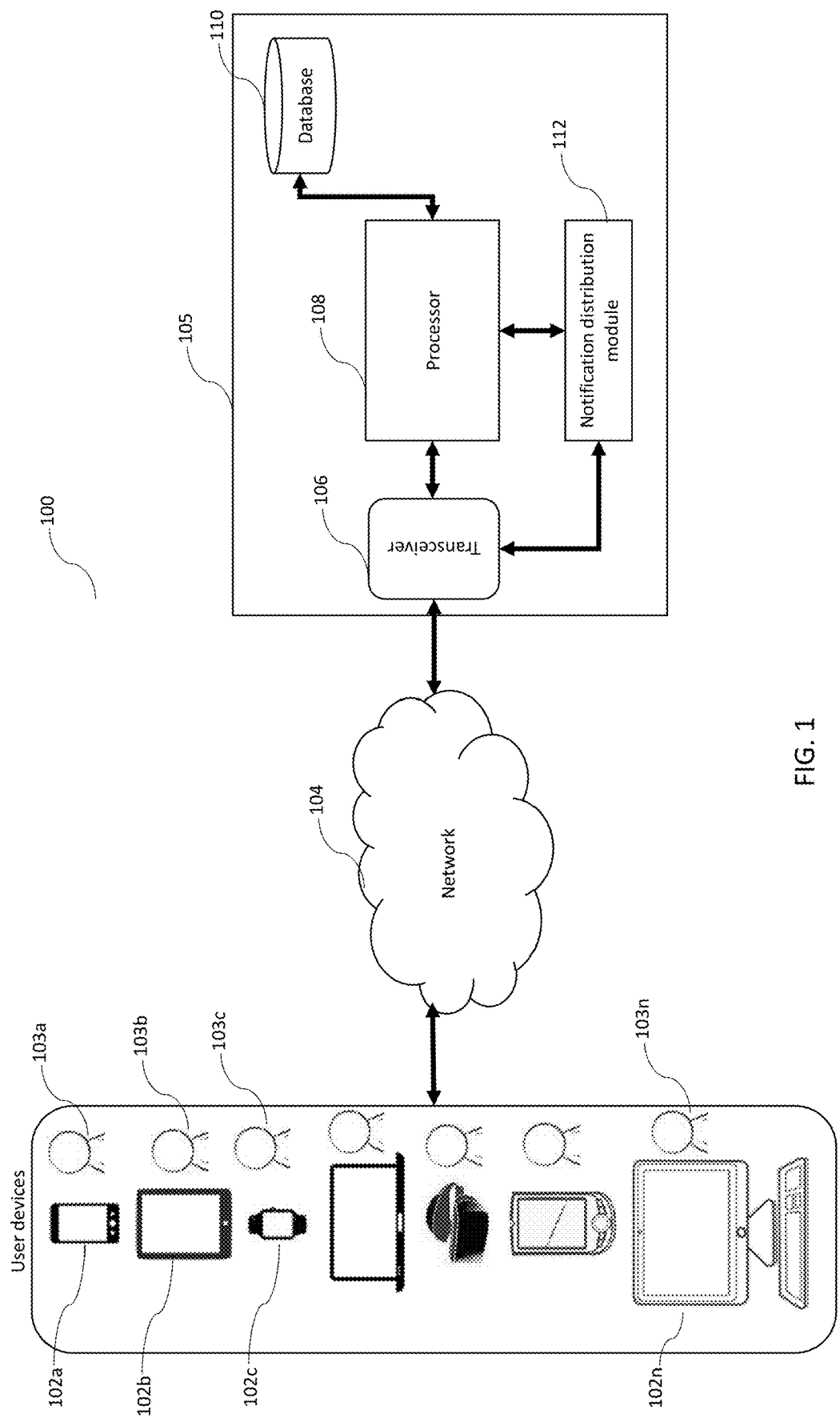
FIG. 1 illustrates a system, in accordance with aspects of the embodiments.

FIG. 1 illustrates a system 100, in accordance with aspects of the embodiments, a block diagram of a system 100 for personalized care/resident management, is illustrated in accordance with an embodiment. The system 100 may include one or more of a processor, memory that includes a temporary transient (volatile) memory such as Random-Access Memory (RAM) and a computer readable medium or article (not shown in FIG. 1).

The system 100 includes a plurality of user devices 102a-102n (collectively referred to as 102) corresponding to a plurality of users 103a-103n (collectively referred to as 103). Each of the users 103 have at least one corresponding user device 104 registered. In other implementations, the user 103 may have multiple user devices registered. Also, each of the user may have a specific role assigned to the user 103 or a profile. The system further includes a central controller 105. The central controller 105 is connected to the plurality of user devices 102 through a network 104.

The central controller 105 may further include a transceiver 106, a processor 108, a notification distribution module 112 and a database 110.

In an implementation, the specific role assigned to the user may be a doctor, a nurse, an attendant, a medicine administrator, or a family member/relative.

In another implementation, the network 104 may be a wireless network, a wired network, or a combination thereof. The network 104 can be implemented as one of the different types of networks, such as intranet, local area network (LAN), wide area network (WAN), the internet, and the like. The network 104 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 104 may include a variety of network devices, including routers, bridges, servers, computing devices, storage devices, and the like.

The central controller 105 may include at least one processor, an input/output (I/O) interface and a database 110. The at least one processor may be implemented as one or more microprocessors, microcomputers, microcontrollers, digital signal processors, central processing units, state machines, logic circuitries, and/or any devices that manipulate signals based on operational instructions. Among other capabilities, the at least one processor is configured to fetch and execute computer-readable instructions stored in the database 110.

The database 110 may either be a primary memory or a secondary memory. For example, but not restricted to, random access memory (RAM), cache memory, hard disk drive (HDD), solid state drive (SSD), compact disk (CD), portable memories, and like.

By way of an example, the system 100 may be a system to access resident's details by the plurality of users 103. Each of the users out of the plurality of the users 103 may login to a same information backplane. The information backplane may be of an assisted living home, a hospital, or any other similar patient managing place. However, it may be apparent to a person having ordinary skill in the art to apply the system as described in any other implementation with similar characteristics.

Still referring to FIG. 1 each of the plurality of users 103 (user and plurality of user will be interchangeably referred as 103) has at least one user device. Each user device 103 may have a software application that needs to be installed on the user device 103. The software application may be an Android application or an iOS application, a windows application, or any other user device application or a web application. A user interface is presented to the user once the user 103 accesses it. The user interface may be accessed using touch or web interface. User 103, may have to enter login credentials that may include a user ID and a password. The database 110 may store multiple user ID and passwords that may have been collected at the time of registration of the user 103. The user 103 may have at least one user device registered. The database 110 may also include profile of the user 103 that may further include a specific assigned role to the user 103. The specific assigned role helps in determining access that the user 103 might have to information on user interface. The profile of the user 103 may also help in identifying to what all information does the user 103 has access.

Once the user 103, wanting to access details of one or multiple residents, may input login credentials on the user interface, this information is sent to the central controller 105. As disclosed earlier, the user device 104 and the central controller may be connected through the network 104. The central controller 105 receives the login credentials of the user 103 through a transceiver 106. The transceiver 106 may be connected to the processor 108. The received login credentials may be forwarded by the transceiver 106 to the processor 108. The processor 108, may query the database to check and authenticate the user. In case the login credentials do not match, the processor 108 may send a notification message describing authentication failure, through the transceiver 106, that may be displayed on the user interface. However, in case the login credentials provided match with the details on the database 110, the processor 108 may then fetch the profile of the user 103. The profile of the user 103 may include details about specific role assigned, the devices the user is allowed access to (e.g. shared mobile device, web computer, personal mobile device, etc.), the times the user is allowed access to the system (e.g. in a shift based environment user may not be allowed to access the system if they are not the shift schedule). In another implementation user device 104 may be a shared device wherein a person may use the device 104 for some time and then handover to other person. Based on the specific role assigned or based on the profile of the user 103, the processor 108, may then provide an information read/write layout. The data presentation within the information read/write layout may be modified with changing users and their assigned specific roles or profiles. For e.g. the information read/write layout for a doctor may have more information to read or write than a nurse who may have access to only profile data of a resident or medication data. Hence, as per the profile of the user 103, landing page and other related information displayed on the information read/write layout and its display may change.

Still referring to FIG. 1, the processor 108 (or the processing module 108) is also connected to the notification distribution module 112. If the user 103, after logging in to the information read/write layout performs certain operation or interacts with the data, there may be a notification that may be generated by the processor 108. The notification may either be a knowledge item that is, it only contains read information. Further, the notification may have an actionable item that the user 103 may have suggested or instructed for a second user. This notification is then communicated by the notification distribution module 112 to corresponding user device of another user. The notification distribution module 112 may format the notification based on a plurality of factors. The format of the notifications may be based on type of notifications being opted, destination user of the notification, time of the notification, location of the destination user, or type user device registered for receiving notifications. Based on the information of all these factors, the notification distribution module 112 may format the notifications in a such a manner so as to keep data private. Therefore, if user to whom the notification is to be delivered, is in a public place as per his location details then complete information is not sent. Only an indicative information is forwarded. So, for e.g. if the user 103 wants to send a notification to a family member/relative of a resident, he may send it through the information read/write layout. However, the notification may have such information that may not be displayed completely in a public place as some other person might see it and hence compromise data security. Therefore, the information is sent in an indicative manner to inform the relative that something has happened to the resident without disclosing name etc. This message can be comprehended by the relative itself.

Figure 2:
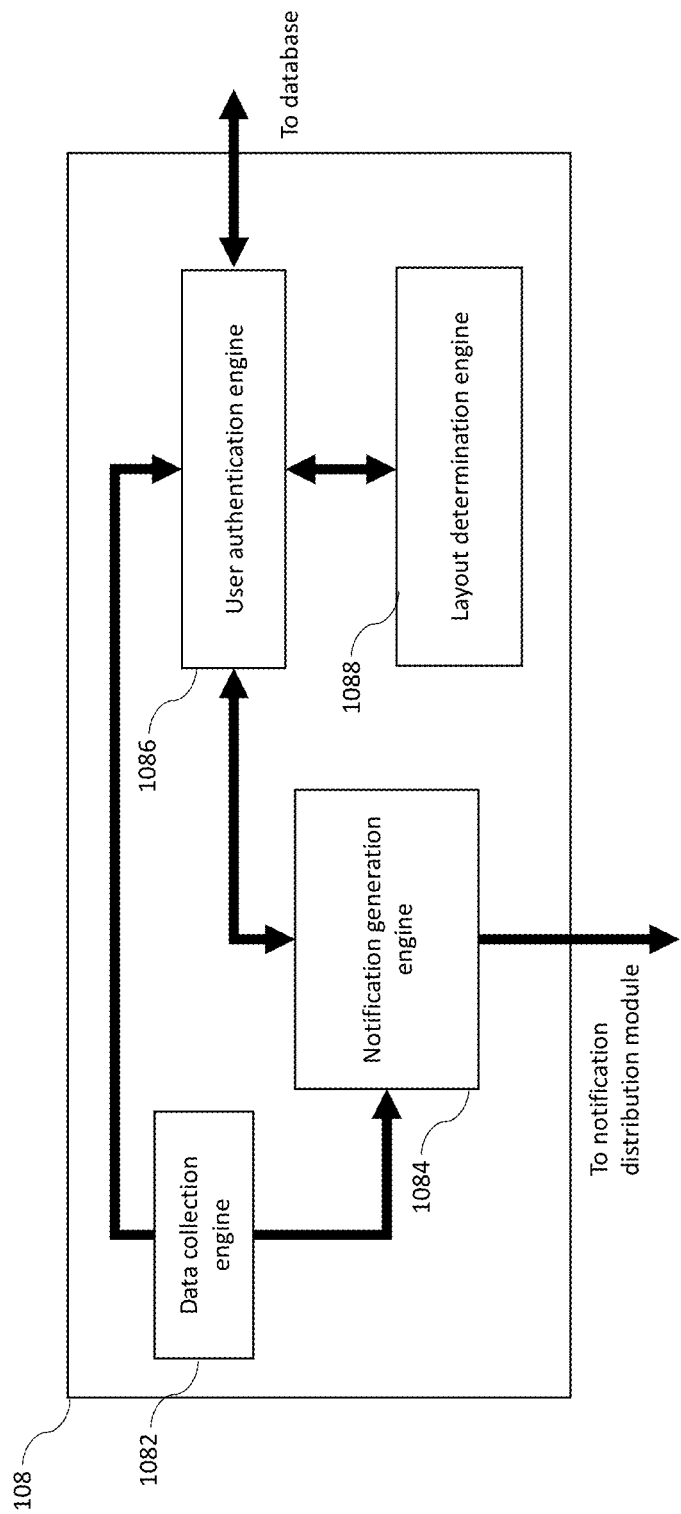
FIG. 2 is a diagram illustrating components within a processor, in accordance with aspects of the embodiments.

Referring now to FIG. 2, a diagram illustrating internal components or modules within the processor 108. The processor 108 may include a data collection engine 1082, a user authentication engine 1086, a layout determination engine 1088 and a notification generation engine 1084.

The data collection engine 1082, may receive data from the transceiver 106 of the central controller 105. The data collected may include user login credentials, location data, device used, time of login, etc. the data collection engine 1082 may make a local repository (not shown in the figure). The local repository may store the data collected for further use. A part of data collected may be forwarded to the user authentication engine 1086 and other part may be forwarded to the notification determination engine 1084 simultaneously. The user authentication engine 1086 may receive the part with the user credentials and communicates with the database 110 of the central controller 105. The user credentials received may be cross checked by the user authentication engine 1086 with the database 110. In case the user credentials are wrong, a display notification of user authentication failure may be sent via the transceiver 106 to user interface of the user device 102. Authentication of a user may also be based on approved or registered devices, device determined to be used, or on specific timing a user is supposed to login. In case, the user credentials or other data as described above are authenticated, profile of the user 103 is also retrieved by the user authentication engine. The profile may be then forwarded simultaneously to the layout determination engine 1088 and the notification generation engine 1084. The layout determination engine 1088, as per the received profile and specific role information within the profile, may modify information and presents the information read/write layout to the user 103 on the user interface of the user device 104. Further, the notification generation engine 1084 may continuously monitor user's activity on the information read/write layout. When the user 103 interacts with the information read/write layout in a manner that may need a follow up interaction of another user, a notification may be automatically generated. In another implementation, the notification may be generated by action of the user 103.

By way of an example in the case of a fall of an individual, a notification is sent to the care givers, another notification sent to administrator, a $3^{rd}$ notification is sent to the family. By way of another example, in case a doctor logged in wants a follow up on effect a prescribed medicine prescribed may generate two notifications automatically. One notification may be generated and may require a nurse to keep noting medicine effect on the resident that the nurse may have to update periodically. While the second notification may be for the medicine administrator who will have to administer the prescribed medicine. In other implementation, a third notification may also be generated for the relative of the resident indicating new medicine prescribed. Hence, the first two notifications may be due to an actionable item needed to be performed by other users and the third notification may be due to an information item needed to be provided to another user. Also, the plurality of users 103 may be arranged in a hierarchical order. The hierarchical order may describe the information read/write layout access. The person at the top of the hierarchy may have access to all the information. The person at the bottom of the order may have only read access of the data.

The notification generation engine 1084 may also monitor the generated notifications and the actionable item attached to the notification. In case, there is an actionable item generated for a second user that is not completed within a certain time limit, the notification generation engine 1084 may generate a second notification to a third user who is above in hierarchy from the second user. Time limit may be user defined or system defined. System may be able to read information and set up a time limit for the actionable item itself.

Figure 3:
FIG. 3 is a table illustrating information layout accessibility, in accordance with aspects of the embodiments.

Now referring to FIG. 3, illustrates a table depicting information layout accessibility. The accessibility may be based upon the user role in the system 100. For e.g. the doctor may have access to full information and full rights of read/write operations. Whereas, an attendant may only have a partial access that may include only read access. The table may also define the hierarchy order within the system 100 to define read/write rights.

Figure 4:
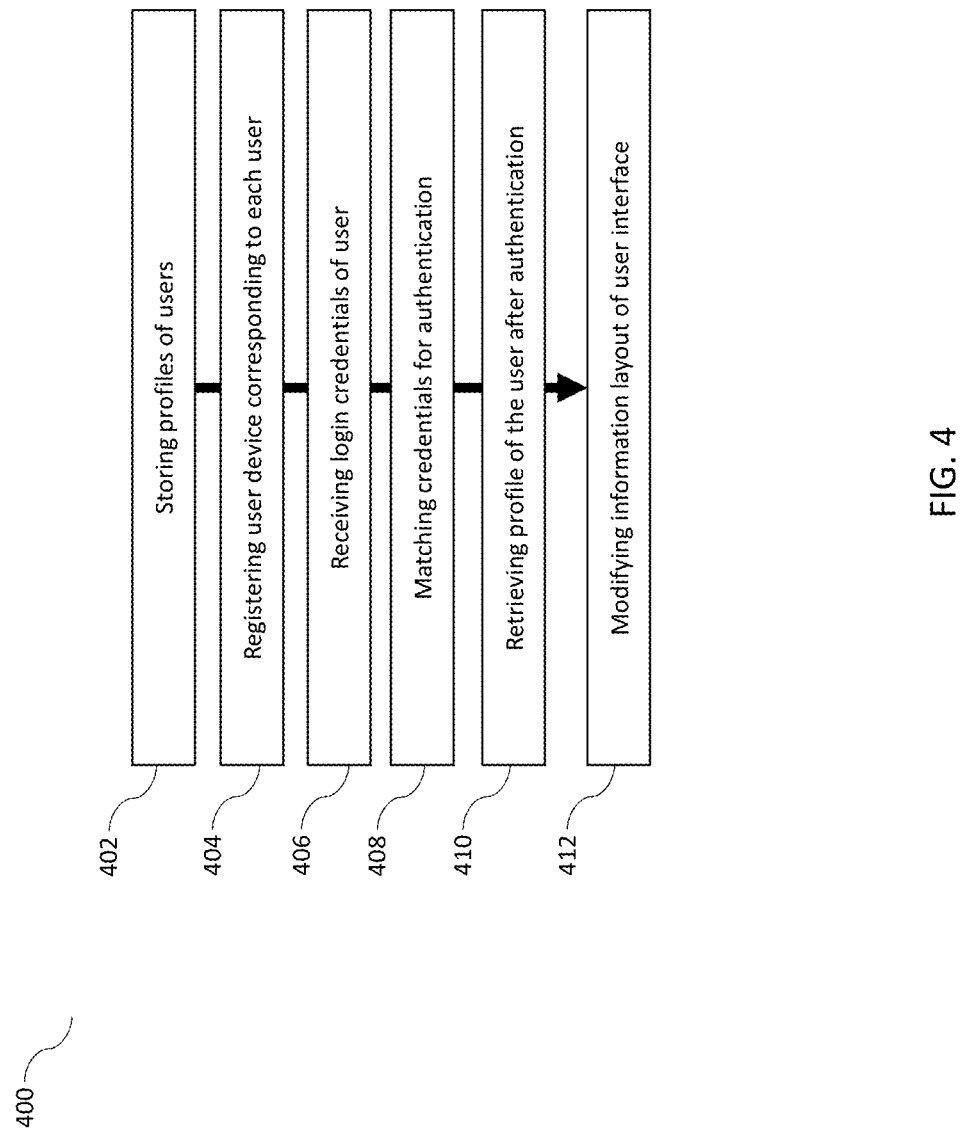
FIG. 4 is a flow chart diagram illustrating overall method of care/resident management tracking, in accordance with an aspect of the embodiments.

Now referring to FIG. 4, illustrating a flowchart method 400 for personalized care/resident tracking. At step 402, the central controller 105 stores profiles of the plurality of users 102. The profile may include data like hierarchical rank, location data, specific role, user device, etc. The profile may be stored within the database 110. In an implementation, this profile may be either collected while registration of the user 103. In other implementation, the profile may be automatically collected. For e.g. location data, user device type, etc.

At step 404, a corresponding user device for the user 103 is also registered along with user registration. At step 406, the central controller 105 receives login credentials of the user 103. The credentials are received through the user interface presented on the user device 102. The user interface, presented on the user device 102, may be through a software application installed on the user device, or through a web interface. Further, at step 408, authentication of the received user credentials is done. The received user credentials are matched with the user's data stored within the database 110. In case the authentication fails, the user 103 receives an "authentication failed" notification displayed on display of the user interface. However, on a successful match, the processor 108, at step 410, retrieves the profile of the user 103. The retrieved profile may include the accessibility data or specific assigned role for the user 103. Based on the specific role assigned to the user 103, the information read/write layout is modified at step 412. That is the information to be presented to a specific type of user depends upon the specific role of a user. Hence, a doctor may have a different layout presented when compared to a nurse or a relative.

Figure 5:
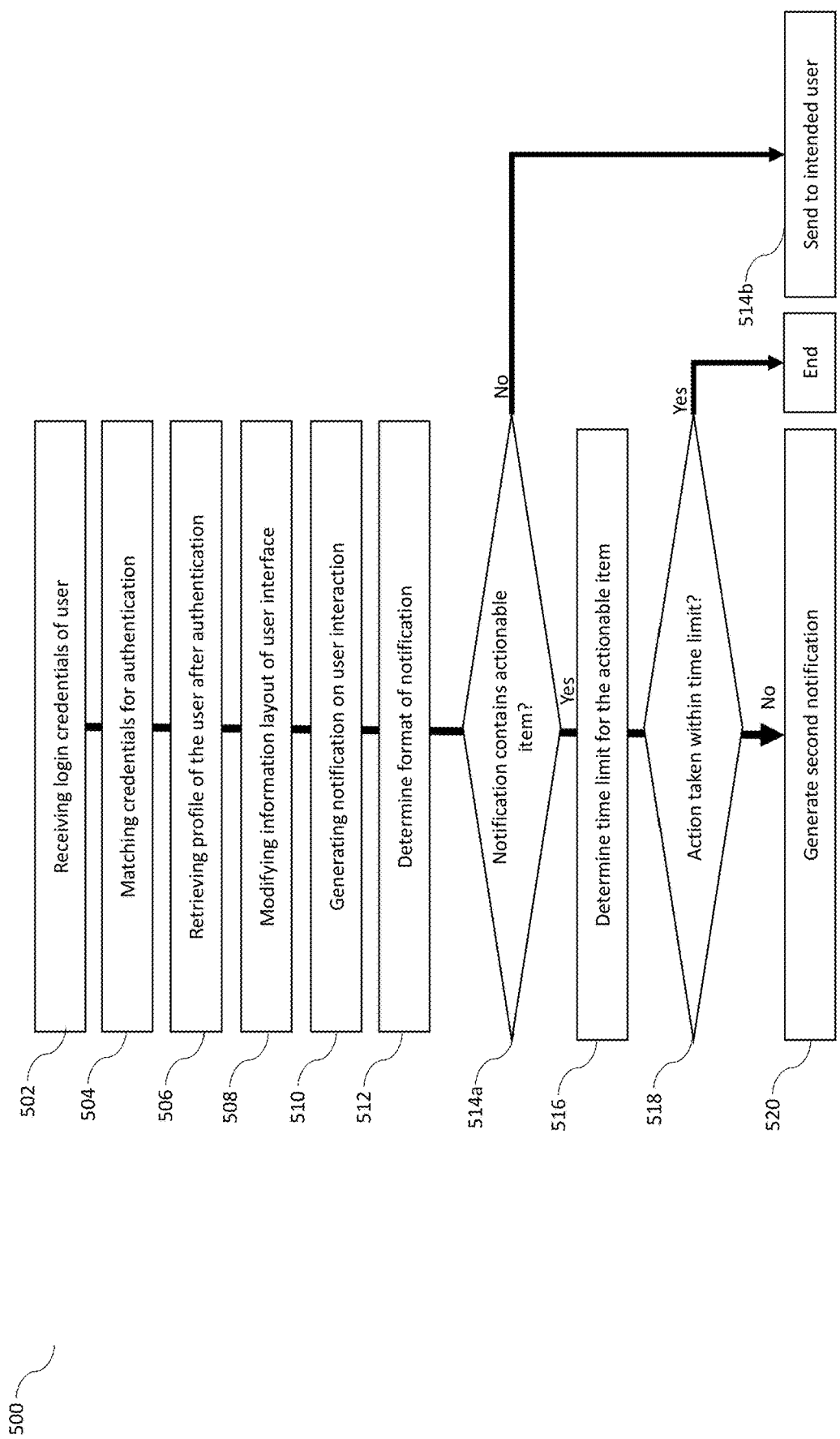
FIG. 5 is a flow chart diagram illustrating method generating second notifications for care/resident management tracking, in accordance with an aspect of the embodiments.

Now referring to FIG. 5, a flow chart illustrating a method 500 to generate second notifications is disclosed. At step 502, the processor 108, receives login credentials of the user 103. The credentials are collected through the interface of the software application initiated by the user 103. The credentials are sent through the network 104 and received by the transceiver 106 that forwards the details to the processor 108. The processor 108, then at step 508, matched the received credentials with the credentials stored in the database 110. On a successful authentication the processor 108, at step 506, retrieves the profile of the user 103. The retrieved profile may include the accessibility data or specific assigned role for the user 103. Further, at step 508, the processor 108 modifies the information read/wrote layout as per the profile of the user 103. If the user 103, interacts with the information read/write layout in any manner, then at step 510, the processor 108 generates the notification. The notification may be an actionable item or an information item intended for the second user. At step 512, the notification distribution module 112, connected to the processor 108, may determine format of the notification generated. As also disclosed above, the format of the notifications may be based on type of notifications being opted, destination user of the notification, time of the notification, location of the destination user, or type user device registered for receiving notifications. Based on the information of all these factors, the notification distribution module 112 may format the notifications in such a manner so as to keep data private.

At step 514a, the processor determines, whether the generated notification has an actionable item or not. In case, the notification only has a knowledge item, then at step 514b, the notification is sent intended user to be displayed on his user device. The format of the notification is based on the format as decided by the notification distribution module 112 as described above. However, in case the notification includes an actionable item, then at step 516, the processor determines time limit, if mentioned or desired, within which the actionable item needs to be performed. Further, at step 518, the processor may keep a check that whether the actionable item has been taken care of or not by the second user. In case the actionable item has been attended to by the second user, the method may be ended and a new process may be started. However, in case the second user has not taken care of the actionable item within the time limit prescribed by the first user or by processor, then the notification generation engine 1084 may generate a second notification for third user at step 520. As described above the plurality of users 103 may be arranged in a hierarchy. Hence, the third user is higher in hierarchy than the second user.

Figure 6:
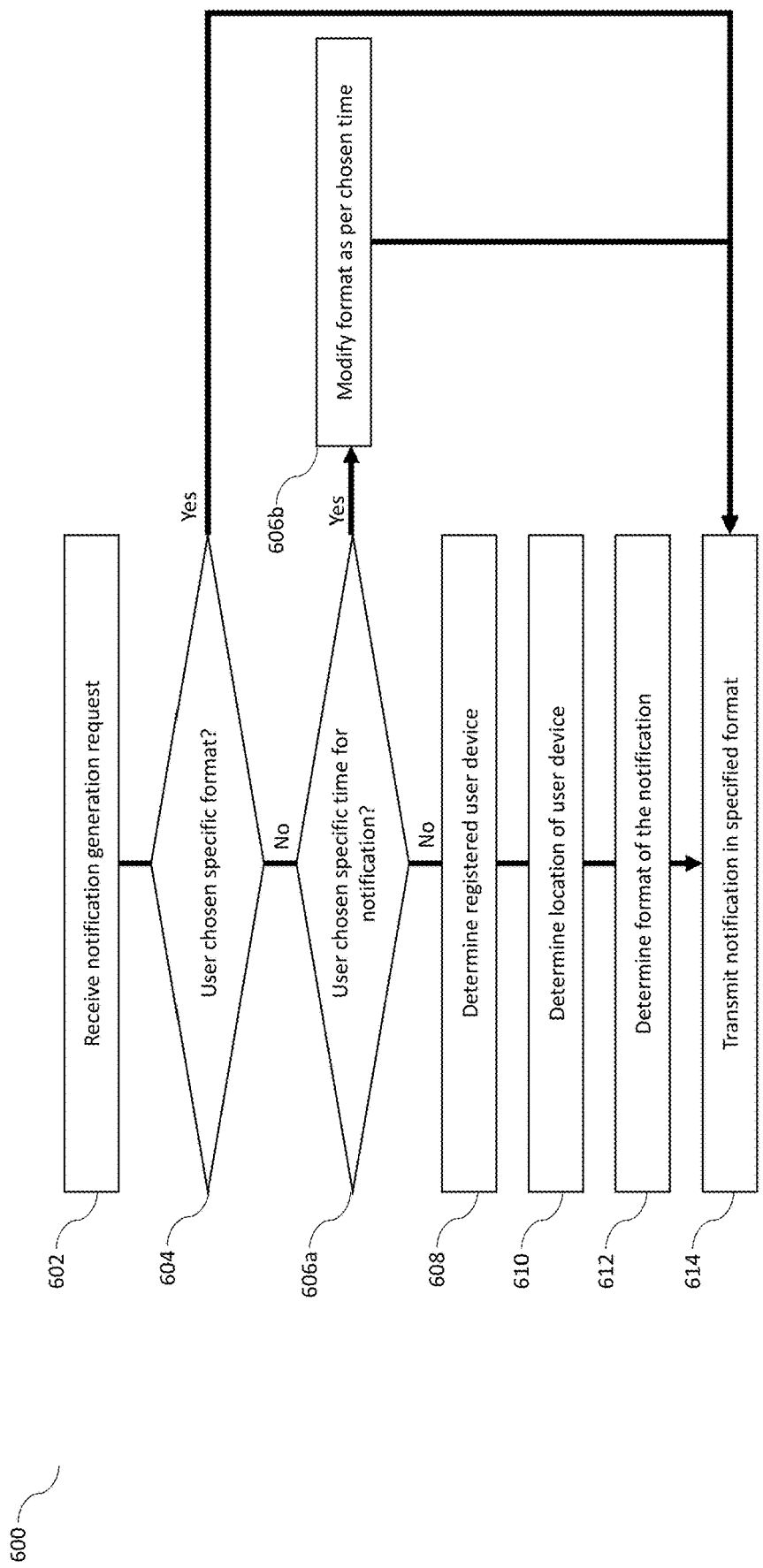
FIG. 6 is a flow chart diagram illustrating modifying notifications formats, in accordance with an aspect of the embodiments.

Now referring to FIG. 6, illustrating a flow chart depicting a method 600 to modify notification formats, in accordance with an aspect of the embodiments. As disclosed above format of the notifications may be based on type of notifications being opted, destination user of the notification, time of the notification, location of the destination user, or type user device registered for receiving notifications. In an implementation, notifications may be like medication being refused by a resident, a fall by a resident, supplies provided by the family being run out, resident out of medication, visitor coming to see a resident, a physician doing a check up on a resident, etc. In another implementation, the notifications may also be based on the timing of use of the shared device 104. In another implementation users may "check out" a device 104 and use it during the course of a shift. The device 104 in use may be different at different times or days. It may be correctly determined on what device 104, the notification should be sent to, based on what shared device is being used.

Based on the information of all these factors, the notification distribution module 112 may format the notifications in a such a manner so as to keep data private. Therefore, if user to whom the notification is to be delivered, is in a public place as per his location details then complete information is not sent. Only an indicative information is forwarded. So, for e.g. if the user 103 wants to send a notification to a family member/relative of a resident, he may send it through the information read/write layout. However, the notification may have such information that may not be displayed completely in a public place as some other person might see it and hence compromise data security. Therefore, the information is sent in an indicative manner to inform the relative that something has happened to the resident without disclosing name etc. This message can be comprehended by the relative itself.

Referring back to FIG. 6, at step 602 the notification generation engine 1084 may receive a notification generation request. The notification may be generated when user 103 interacts with the information read/write layout. In an implementation, the notification may be generated by system 100 itself. For e.g. when medication time for the patient has elapsed above a threshold time, a notification may be generated for the medication assistant.

Further at step 604 a check is done determining whether the user 103 has chosen any specific format or not. If the user 103 has a specific format set for the notification, the notification may be then sent to the user 103 in that specified format at step 614.

However, in case there is no specific format chosen by the user 103, then at step 606a, the notification distribution module 112 may determine whether there is any specific time chosen by the user 103. In case there is a specific time chosen by the user 103, then at step 606b format of the notification is modified as per the time of the day. For e.g. in case the time for notifications chosen by the user is a time that generally falls after office hours or at a time that generally falls when the user 103 may be alone, then the notification is modified as per the time. In an implementation, notifications may be sent out at all times, e.g. urgent notifications. Urgent notification may be on the occasion of a fall, or a resident being sent to a hospital. In case, the user 103 has not chosen any specific time, then at step 608, the notification distribution module determines the registered device for the user 103. The registered user device may be categorized further as a home device, shared device or out of home device or any other category of device. At step 610, the location of the user device is determined. Location details may be collected from location capturing components of the user device. Various devices include GPS chips to identify and collect location details. These details may be collected by communicating with the user device 102 or while the user 103 logs in to the system 100. The processor 108 may identify the location as residence or public place in relation to time. At step 612, the notification module 112 determines the format of the notification. Therefore, if user to whom the notification is to be delivered, is in a public place as per his location details then complete information is not sent. Only an indicative information is forwarded. So, for e.g. if the user 103 wants to send a notification to a family member/relative of a resident, he may send it through the information read/write layout. However, the notification may have such information that may not be displayed completely in a public place as some other person might see it and hence compromise data security. Therefore, the information is sent in an indicative manner to inform the relative that something has happened to the resident without disclosing name etc. This message can be comprehended by the relative itself. At step 614, the notification is transmitted in the determined format.

Figure 7:
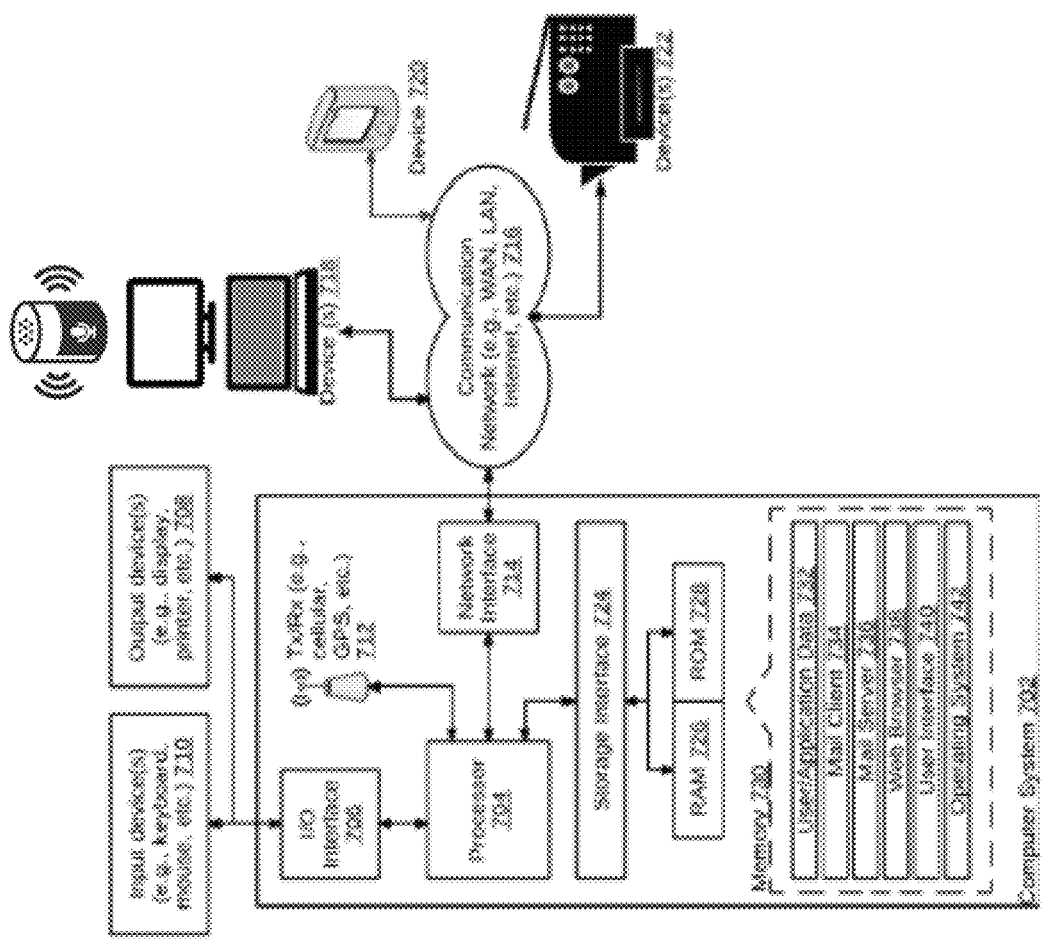
FIG. 7 is a block diagram of an exemplary computer system, in accordance with an aspect of the embodiments.

Now referring to FIG. 7, illustrating a block diagram of an exemplary computer system 702 for implementing various embodiments is disclosed. Computer system 702 may comprise a central processing unit ("CPU" or "processor") 704. Processor 704 may comprise at least one data processor for executing program components for executing user- or system-generated requests. A user may include a person, a person using a device such as such as those included in this disclosure, or such a device itself. Processor 704 may include specialized processing units such as integrated system (bus) controllers, memory management control units, floating point units, graphics processing units, digital signal processing units, etc. Processor 704 may include a microprocessor, such as AMD Athlon, Duron or Opteron, ARM's application, embedded or secure processors, IBM PowerPC, Intel's Core, Itanium, Xeon, Celeron or other line of processors, etc. Processor 704 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

Processor 704 may be disposed in communication with one or more input/output (I/O) devices via an I/O interface 706. I/O interface 706 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using I/O interface 706, computer system 702 may communicate with one or more I/O devices. For example, an input device 708 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc. An output device 710 may be a printer, fax machine, video display (e.g., cathode ray tube (CRT), liquid crystal display (LCD), light-emitting diode (LED), plasma, or the like), audio speaker, etc. In some embodiments, a transceiver 712 may be disposed in connection with processor 704. Transceiver 712 may facilitate various types of wireless transmission or reception. For example, transceiver 712 may include an antenna operatively connected to a transceiver chip (e.g., Texas Instruments WiLink WL1283, Broadcom BCM4760IUB8, Infineon Technologies X-Gold 618-PMB9800, or the like), providing IEEE 802.11a/b/g/n, Bluetooth, FM, global positioning system (GPS), 2G/3G HSDPA/HSUPA communications, etc.

In some embodiments, processor 704 may be disposed in communication with a communication network 714 via a network interface 716. Network interface 716 may communicate with communication network 714. Network interface 716 may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. Communication network 714 may include, without limitation, a direct interconnection, local area network (LAN), wide area network (WAN), wireless network (e.g., using Wireless Application Protocol), the Internet, etc. Using network interface 716 and communication network 714, computer system 702 may communicate with devices 718, 720, and 722. These devices may include, without limitation, personal computer(s), server(s), fax machines, printers, scanners, various mobile devices such as cellular telephones, smartphones (e.g., Apple iPhone, Blackberry, Android-based phones, etc.), tablet computers, wearable device such as a smart watch, eBook readers (Amazon Kindle, Nook, etc.), laptop computers, notebooks, gaming consoles (Microsoft Xbox, Nintendo DS, Sony PlayStation, etc.), or the like. In some embodiments, the computer system 602 may itself embody one or more of these devices.

In some embodiments, processor 704 may be disposed in communication with one or more memory devices (e.g., a RAM 726, a ROM 728, etc.) via a storage interface 724. Storage interface 724 may connect to memory devices 730 including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc.

Memory devices 730 may store a collection of program or database components, including, without limitation, an operating system 732, a user interface application 734, a web browser 736, a mail server 738, a mail client 740, a user/application data 742 (e.g., any data variables or data records discussed in this disclosure), etc. Operating system 732 may facilitate resource management and operation of computer system 702. Examples of operating system 732 include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like. User interface 734 may facilitate display, execution, interaction, manipulation, or operation of program components through textual or graphical facilities. For example, user interfaces may provide computer interaction interface elements on a display system operatively connected to computer system 702, such as cursors, icons, check boxes, menus, scrollers, windows, widgets, etc. Graphical user interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, computer system 702 may implement web browser 736 stored program component. Web browser 736 may be a hypertext viewing application, such as Microsoft Internet Explorer, Google Chrome, Mozilla Firefox, Apple Safari, etc. Secure web browsing may be provided using HTTPS (secure hypertext transport protocol), secure sockets layer (SSL), Transport Layer Security (TLS), etc. Web browsers may utilize facilities such as AJAX, DHTML, Adobe Flash, JavaScript, Java, application programming interfaces (APIs), etc. In some embodiments, computer system 702 may implement mail server 738 stored program component. Mail server 738 may be an Internet mail server such as Microsoft Exchange, or the like. Mail server 738 may utilize facilities such as ASP, ActiveX, ANSI C++/C#, Microsoft .NET, CGI scripts, Java, JavaScript, PERL, PHP, Python, WebObjects, etc. Mail server 738 may utilize communication protocols such as internet message access protocol (IMAP), messaging application programming interface (MAPI), Microsoft Exchange, post office protocol (POP), simple mail transfer protocol (SMTP), or the like. In some embodiments, computer system 702 may implement mail client 740 stored program component. Mail client 740 may be a mail viewing application, such as Apple Mail, Microsoft Entourage, Microsoft Outlook, Mozilla Thunderbird, etc.

In some embodiments, computer system 702 may store user/application data 742, such as the data, variables, records, etc. as described in this disclosure. Such databases may be implemented as fault-tolerant, relational, non-relational, scalable, secure databases such as Microsoft SQL server, Oracle, NoSQL, grpahy or Sybase. Alternatively, such databases may be implemented using standardized data structures, such as an array, hash, linked list, struct, structured text file (e.g., XML), table, or as object-oriented databases (e.g., using ObjectStore, Poet, Zope, etc.). Such databases may be consolidated or distributed, sometimes among the various computer systems discussed above in this disclosure. It is to be understood that the structure and operation of the any computer or database component may be combined, consolidated, or distributed in any working combination.

Figure 8:
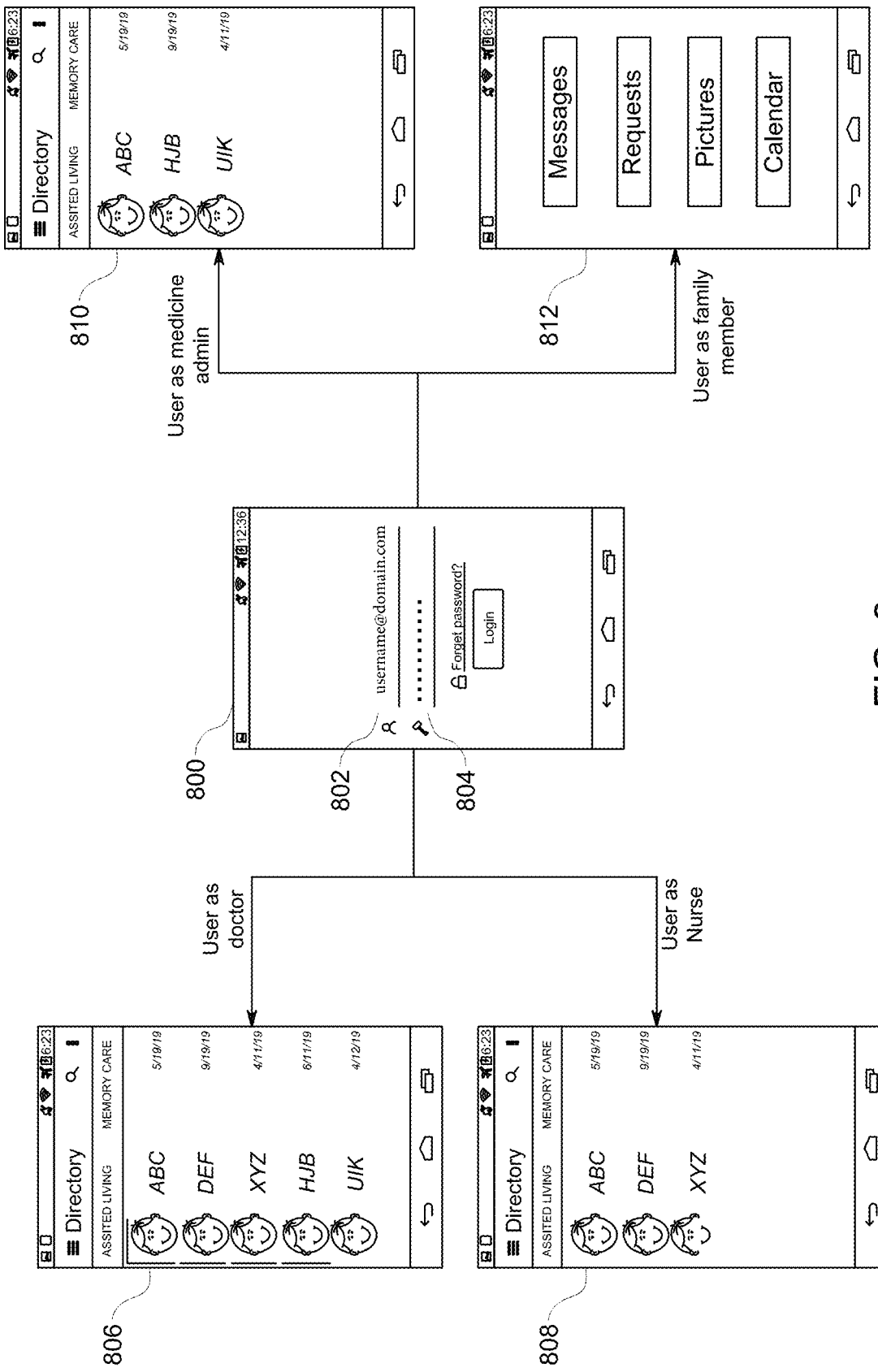
FIG. 8 is a diagram illustrating various user interfaces for users with different roles, in accordance with an aspect of the embodiments.

Now referring to FIG. 8, illustrating various user interfaces for users with different roles, in accordance with an aspect of the embodiments. As discussed above, the information read/write layout is modified as per the specific role or profile of the plurality of users 103. The user interface 800 is an exemplary login page for a mobile phone. Similar user interfaces may be provided on any type of user device. The user interface 800 may be generated when the user 103 activates a software application on the user devices or opens up a web page for the same. The user interface 800 includes a username field 802 and a password field 804. In other implementation, user login may also be biometric based like fingerprints, pulse or other biosensor related data that may be processed as a bio-print. After logging in with registered credentials, the user 103 may be authenticated. On authentication, the profile of the user 103 is accessed. Based on the user profile, specific role of the user is determined and the layout determination engine 1088 determines the information read/write layout of the user interface 800. If the user 103 is a doctor, the information read/write layout is as shown by user interface 806. This layout may display all residents or patients available and mapped to the doctor. User interface 808, displays information read/write layout if the user 103 is logged in is a nurse. Noticeable is the difference between the user interface 806 and user interface 808. Number of residents may be different. Further, user interface 810 displays user interface if the user 103 logged in is a medicine administrator. Similarly, if the user 103 is a family member/relative, the user interface 812 is presented.

Figure 9:
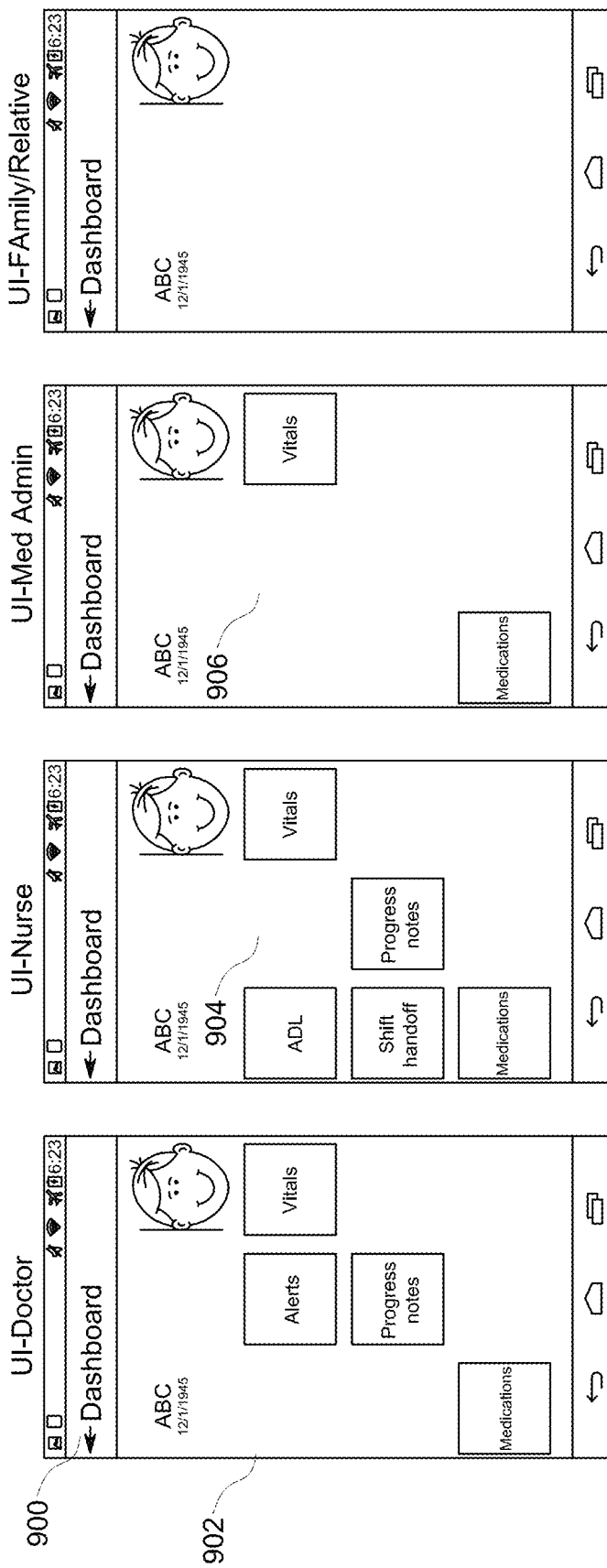
FIGS. 9A-9D are diagrams illustrating various information dashboards for various user with different roles, in accordance with an aspect of the embodiments.

FIGS. 9a-9d illustrates various user interface dashboard 900 based on specific roles assigned to users. As disclosed in FIG. 9a, the dashboard 900 has items field 902 based on the user 103 being a doctor. As may be observed, the items presented in items field 902 are many in number and hence may be only presented to a doctor. Further, as shown in FIG. 9b, the items field 904 displays a little less information as the user 103 logged in is a nurse. Similarly, the items field 906 depicted in FIG. 9c and items field 908 depicted in FIG. 9d may be presented for the user 103 being a medicine administrator and a family member/relative respectively. The change in the items in the items fields 902, 904, 906, and 908 may be observed. The change in the items is due to the specific role of the user 103 logged in to the system 100.

Figure 10:
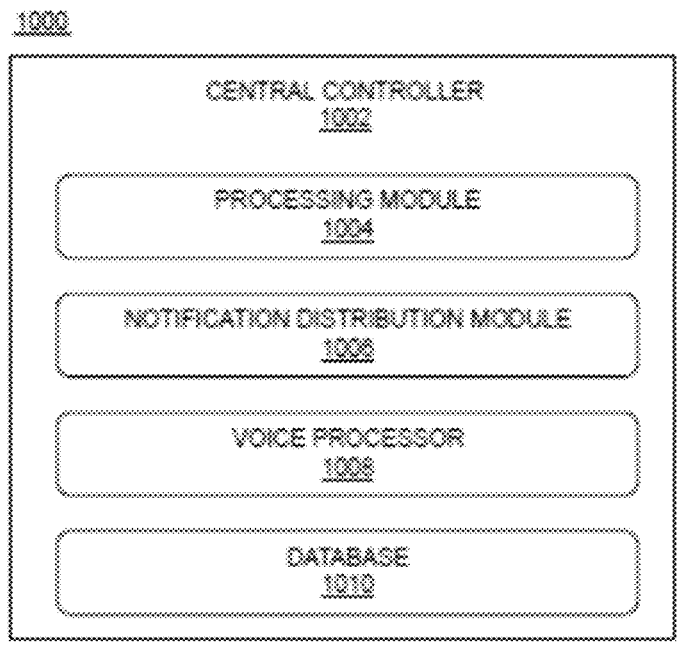
FIG. 10 is a block diagram illustrating system elements of a central controller of a communication system, in accordance with an embodiment of the present disclosure.

FIG. 10 is a block diagram 1000 illustrating system elements of a central controller 1002 of a communication system, in accordance with an embodiment of the present disclosure. As shown, the central controller 1002 includes a processing module 1004, a notification distribution module 1006, a voice processor 1008, and a database 1010.

The communication system includes a plurality of user devices corresponding to a plurality of users. Each user of the plurality of users has a specific assigned role. Further, each user device of the plurality of user devices presents an interactive user interface to the corresponding user. Non-limiting examples of the plurality of user devices may include a television, a smartphone, a tablet computer, a smart watch, a fitness tracker, a laptop computer, a desktop computer, a personal digital assistant, a smart television, or a wearable device. Further, the network may be a wired or a wireless network. Examples of the wireless network may include, but are not limited to, a mobile network, a satellite network, a Wi-Fi, or a Wireless local area network (WLAN).

The central controller 1004 is connected to the plurality of user devices through a network. The central controller 1004 includes the processing module 1004 configured to receive login credentials of the user through the user interface. The processing module 1004 may be implemented as one or more microprocessors, microcomputers, microcontrollers, digital signal processors, central processing units, state machines, logic circuitries, and/or any devices that manipulate signals based on operational instructions. Among other capabilities, the processing module 1004 is configured to fetch and execute computer-readable instructions stored in the database 1010.

The database 1010 may either be a primary memory or a secondary memory. For example, but not restricted to, random access memory (RAM), cache memory, hard disk drive (HDD), solid state drive (SSD), compact disk (CD), portable memories, and like.

By way of an example, the communication system may be a system to access resident's details by the plurality of users. Each of the users out of the plurality of users may login to a same information backplane. The information backplane may be of an assisted living home, a hospital, or any other similar patient managing place. However, it may be apparent to a person having ordinary skill in the art to apply the system as described in any other implementation with similar characteristics.

Each of the plurality of users has at least one user device. Each user device may have a software application that needs to be installed on the user device. The software application may be an Android application or an iOS application, a windows application, or any other user device application or a web application. A user interface is presented to the user once the user accesses it. The user interface may be accessed using touch or web interface. User may have to enter login credentials that may include a user ID and a password. The database 1010 may store multiple user ID and passwords that may have been collected at the time of registration of the user. The user may have at least one user device registered. The database 1010 may also include profile of the user that may further include a specific assigned role to the user. The specific assigned role helps in determining access that the user might have to information on user interface. The profile of the user may also help in identifying to what all information does the user have access.

Once the user, wanting to access details of one or multiple residents, may input login credentials on the user interface, this information is sent to the central controller 1002. As disclosed earlier, the user device and the central controller 1002 may be connected through the network. The central controller 1002 receives the login credentials of the user through a transceiver.

The processing module 1004 is also configured to cross check the login credentials of the user in the database 1010. The processing module 1004 is also configured to retrieve a specific role assigned to the user. The specific assigned role may be based on the type/group of user. In some embodiments, the type of the user may include at least one of a family member, an attendant, a nurse, a doctor, or a medicine administrator. The processing module 1004 may also provide an information read/write layout, subsequent to login based on the specific assigned role of the user. In some embodiments, the information read/write layout allows the user to perform read and write operation.

The notification module 1006 of the central controller 1002 is adapted to generate a first notification addressed to the plurality of users when a user interacts with the user interface. The plurality of users may include one of more groups of users. Further, one group of the users is different from the other group of the users. The user interacts with the user interface through at least one of a voice input, a text input, a video input, and a touch-based input.

The notification module 1006 is further configured to generate a second notification in case actionable item is not attended within a certain time limit based on the first notification by the plurality of users, wherein the second notification is assigned to the next user within the same or different group of users. The notification distribution module may distribute the generated first and second notifications to the plurality of users in different formats based on the profile of the plurality of users, the registered user device(s), or a location of the user determined using location services from the user device. The format of second notification is not changed when the second notification is assigned to the next user within the same group of users. In some embodiments, the format of second notification is changed when the second notification is assigned to the next user of different group of users, other than the group of users the second notification was assigned earlier. Further, the next user to whom the second notification is assigned is always above in hierarchy in the same or different group of users.

In some embodiments, at least one notification is generated based on the user interaction with the user interface. Further, the different formats may be based on the specific assigned role, the type of the user device, or location of the user device.

The voice processor 1008 is configured to receive at least one voice input comprising a request from the user through the user interface, wherein the request of the user may be presented on at least one user device associated with at least one user. In some embodiments, the voice processor 1008 is configured to convert voice into at least one of a text message, and a video message. In an exemplary scenario, the user providing the at least one voice input including a request may be an aged person residing in an old age home or a patient in a hospital, the at least one other user may be a care taker or a nurse. Examples of the request may include such as, but not limited to, "I want to go to the bathroom", "When will the doctor come to check me", "I need food", "I want to meet my son", and so forth. The caretaker or nurse may receive the request on their associated user device like a phone in form of a text message, voice message, video message, a haptic feedback, and so forth.

The voice processor 1008 is also configured to receive one or more voice inputs including a response from the at least one user of the plurality of users, wherein the response of the at least one user is presented on a user device of the user. For example, the caretaker or the nurse may respond through voice response or text response like "I am coming to see you", "doctor will come at 4 PM", "we will inform your son", and so forth. The caretaker or nurse may record a message in their corresponding user device, the voice processor may present the recorded message or the voice response or the text response to the user i.e. the aged person or the patient. In some embodiments, if the user is watching a television, the response from the other user may flash on a part or on full screen of the television.

The database 1010 may store profiles of the plurality of users, profiles of the users, specific roles' information of the users, and so forth.

An embodiment of the present disclosure provides a method for personalized care/resident management. The method includes: storing, in a database, profiles of a plurality of users; registering, in the database, at least one corresponding user device for each of the plurality of users; receiving, by a processing module, login credentials of the user through an interactive user interface on the user device; matching, by the processing module, the login credentials received for authentication; retrieving, by the processing module, a profile of the user post authentication; modifying, by the processing module, information layout of the user interface based on the profile of the user; and generating, by a notification distribution module, a first notification addressed to the plurality of users when the user interacts with the user interface, the plurality of users having one of more groups of users. One group of the users is different from the other group of the users. The user interacts with the user interface through at least one of a voice input, a text input, a video input, and a touch-based input. Further, the method includes generating, by the notification distribution module, a second notification in case actionable item is not attended within a certain time limit based on the first notification by the plurality of users. The second notification is assigned to the next user within the same or different group of users. The method further includes distributing, by the notification distribution module, the generated first and second notifications to the plurality of users in different formats based on the profile of the plurality of users, the registered user device(s), or location of the user determined using location services from the user device. The format of second notification is not changed when the second notification is assigned to the next user within the same group of users. The format of second notification is changed when the second notification is assignment to the next user of different group of users, other than the group of users the second notification was assigned earlier. The next user to whom the second notification is assigned is always above in hierarchy in the same or different group of users. The method also includes: receiving, by a voice processor, at least one voice input comprising a request from the user through the user interface; presenting, by the voice processor, the request of the user on at least one user device associated with at least one user; receiving, by the voice processor, one or more voice inputs comprising a response from the at least one user of the plurality of users; and presenting, by the voice processor, the response of the at least one user on a user device of the user.

In an aspect of the present disclosure, the method also includes converting, by the voice processor, the at least one voice input and the one or more voice inputs into at least one of a text message, and a video message.

In some embodiments, the notification may include at least one of an actionable item, or an information item for the user. Further, in some embodiments, the format of notifications may include at least one of a text message, an e-mail notification, an in-application message, or an in-application notification. The specific assigned role may be based on the type/group of user. The different formats may be based on the specific assigned role, the type of the user device, or location of the user device.

Another embodiment of the present disclosure also provides a non-transitory computer-readable storage medium performing personalized care management, when executed by a computing device, cause the computing device (or user device) to store profiles of a plurality of users; register at least one corresponding user device for each of the plurality of users; receive login credentials of the user through an interactive user interface on the user device; match the login credentials received for authentication; retrieve a profile of the user post authentication; modify information layout of the user interface based on the profile of the user; generate a first notification addressed to the plurality of users when the user interacts with the user interface, the plurality of users having one of more groups of users, wherein one group of the users is different from the other group of the users, wherein the user interacts with the user interface through at least one of a voice input, a text input, a video input, and a touch-based input; generate a second notification in case actionable item is not attended within a certain time limit based on the first notification by the plurality of users, wherein the second notification is assigned to the next user within the same or different group of users; distribute the generated first and second notifications to the plurality of users in different formats based on the profile of the plurality of users, the registered user device(s), or location of the user determined using location services from the user device, wherein the format of second notification is not changed when the second notification is assigned to the next user within the same group of users, wherein the format of second notification is changed when the second notification is assignment to the next user of different group of users, other than the group of users the second notification was assigned earlier, further wherein the next user to whom the second notification is assigned is always above in hierarchy in the same or different group of users; receive at least one voice input comprising a request from the user through the user interface; present the request of the user on at least one user device associated with at least one user; receive one or more voice inputs comprising a response from the at least one user of the plurality of users; and present the response of the at least one user on a user device of the user.

Figure 11:
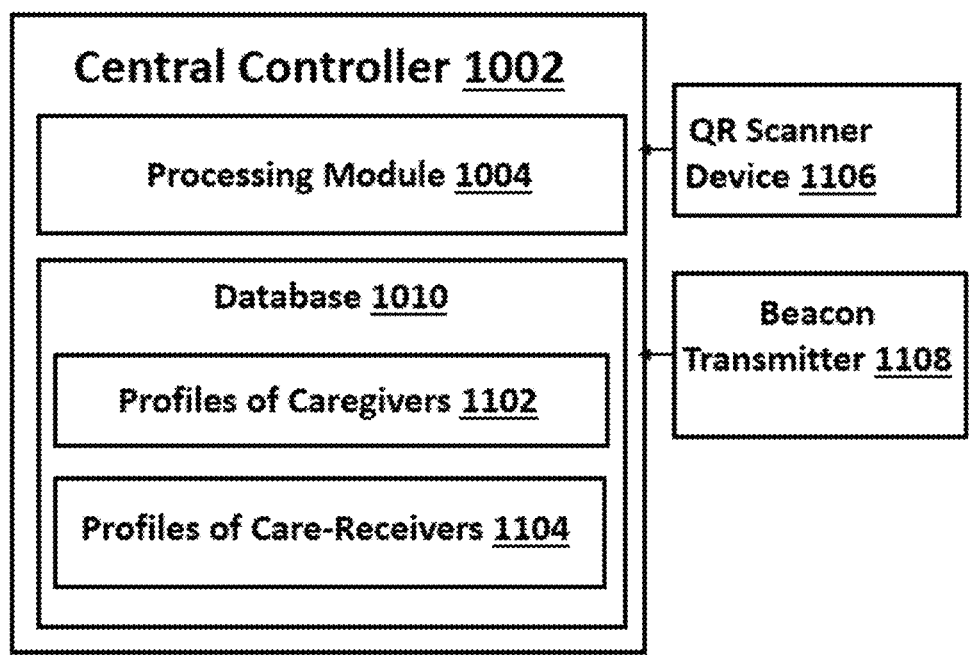
FIG. 11 is a block diagram illustrating system elements of the central controller communicating with external devices to receive input data related to non-scheduled actionable items, in accordance with an embodiment of the present disclosure.

FIG. 11 is a block diagram 1100 illustrating system elements of the central controller 1002 communicating with external devices to receive input data related to non-scheduled actionable items, in accordance with an embodiment of the present disclosure. As shown, the central controller 1002 includes a processing module 1004, a database 1010. The database 1010 may store various data and metadata pertaining to the personalized care management being provided to the care receivers. Accordingly, the database 1010 may store profiles of the authorized caregivers 1102 and profiles of the at least one care receiver 1104 that may be access by the authorized caregivers. The central controller 1002 communicating with external devices including, but not limited to a QR scanner device 1106 and a Beacon Transmitter 1108.

According to one embodiment of the present disclosure, the communication system for providing personalized care management comprises plurality of user devices corresponding to plurality of authorized caregivers, such as a family member of the care receiver, an attendant for the care receiver, a nurse for the care receiver, a doctor for the care receiver, or a medicine administrator for the care receiver, nurses, medical practitioners, friends, etc. Each user device may provide interactive user interface to facilitate the caregiver to provide input data associated with an actionable item being performed for at least one care receiver. The care receiver may include one or more patients, old aged persons, disabled or differently abled persons, dependent adults, dependent minors etc. The database 1010 may store multiple user ID and passwords that may have been collected at the time of registration of the plurality of users. This facilitates in authorizing the users to access the data associated with the personalized care management of the care receivers. The plurality of authorized users may have at least one user device registered with the care management system. The database 1010 may also include profile of the plurality of authorized caregivers 1102 that may further include a specific assigned role to each of the caregivers/users. The specific assigned role helps in determining access that the users might have to information on user interface. The profile of the plurality of authorized caregivers/users may also help in identifying to what all information does a user have access for performing analysis as required for a particular care-receiver. The database 1010 is an integral part of the central controller 1002 and may also be configured for storing profiles of the care receivers 1104. The profiles of the authorized caregivers 1102 are stored in different formats based on specific roles assigned to the authorized caregivers, and location of the plurality of user devices. The profiles of the care-receivers 1104 may include personal details such as name, age, gender of the care-receivers, medical history, diet charts, behavior pattern, physical and mental health condition, etc.

According to one embodiment of the present disclosure, the actionable item may include the actions or events like medical care, psychological care, non-medical care, daily routine care, providing medicines, food and water to the care receivers, measuring vital readings of the care receivers such as blood pressure, blood sugar levels, pulse rate, temperature etc.; providing personal hygiene care, and other services, being provided to the at least one care-receiver by the plurality of authorized caregivers.

In one embodiment of the present disclosure, the actionable item includes one of: a scheduled actionable item and a non-scheduled actionable item. The scheduled actionable item may include providing timely medicines, food, checking blood pressure, blood sugar levels etc., which occurs on fixed schedule or time intervals. The non-scheduled actionable item may include various events or actions that are performed for a care-receiver without following a specific schedule, for example random bathing, frequent urination, work-outs, eating meals/snacks randomly. In other words, the non-schedule actionable items are random actions that may occur any number of times and during any time within twenty-four hours. Thus, the non-scheduled actionable item includes one or more actions which are performed randomly for the care receiver; whereas, the scheduled actionable item includes one or more actions which are performed for the care receiver, according to a schedule prescribed by the corresponding authorized caregivers.

The non-scheduled actionable items are equally important to be recorded, since each recorded events or history, whether it is for a scheduled event or if it is for a random event, will provide a better idea to the care-giver about the condition of the care receiver being attended. Accordingly, the caregiver will be able to better analyze the condition of the care receiver and thereby suggest further recommendations, such as line of treatment, care plan, psychological assistance, diet plan, etc., as appropriate for the care-receivers.

Therefore, both the scheduled actionable items and the non-scheduled actionable items that are being performed for the care receivers, are recorded in the system via the central controller 1002. The central controller 1002 may be communicatively connected to the plurality of user devices through a communication network to facilitate the authorized caregivers to analyze the profiles of the at least one care receiver 1104 from a remote location.

The central controller 1002 also comprises the processing module 1004 that is configured to receive, via the plurality of user devices, the at least one input data based on the scheduled actionable item. The processing module 1004 is also configured to receive, via the plurality of user devices, the at least one input data based on the non-scheduled actionable item. Once the data related to both the scheduled actionable item and the non-scheduled actionable item are recorded or inputted in the processing module 1004, the profile of the at least one care receiver 1104 is thereby based on the received at least one input data. Thereafter, the updated profile of the at least one care receiver 1104 in saved in the database 1010 for future analysis. The authorized caregivers further analyze the updated profile of the at least one care receiver 1104. Subsequently, the caregiver suggests further recommendations, such as line of treatment, care plan, psychological assistance, diet plan, etc. to the care receiver.

Another embodiment of the present disclosure provides a method for providing personalized care/resident management. The method comprises the steps of: configuring a plurality of user devices corresponding to a plurality of authorized caregivers, each user device providing an interactive user interface for: providing input data associated with an actionable item being performed for at least one care receiver, wherein the actionable item includes one of: a scheduled actionable item and a non-scheduled actionable item; configuring a database 1010 for storing profiles of the authorized caregivers 1102 and profiles of the at least one care receiver 1104; configuring a central controller 1002 connected to the plurality of user devices through a communication network for facilitating the authorized caregivers to analyze the profiles of the at least one care receiver from a remote location; configuring a processing module 1004 for: receiving, via the plurality of user devices, the at least one input data based on the scheduled actionable item; receiving, via the plurality of user devices, the at least one input data based on the non-scheduled actionable item; updating the profile of the at least one care receiver 1104 based on the received at least one input data; saving the updated profile of the at least one care receiver in the database 1010; and facilitating the authorized caregivers to further analyze the updated profile of the at least one care receiver 1104.

In one embodiment of the present disclosure, the at least one input data based on the non-scheduled actionable item is inputted into the processing module 1004 through at least one QR Code scanner device 1106. In another embodiment of the present disclosure, the at least one input data based on the non-scheduled actionable item is inputted into the processing module 1004 through at least one Beacon Transmitter 1108. The QR Code Scanner device 1106 and the Beacon Transmitter 1108 receive the digitized data associated with the non-scheduled actionable items. The received data is further inputted into the central controller 1002 for processing by the processing module 1004.

The order in which the method as described above, is not intended to be construed as a limitation, and any number of the described method blocks can be combined in any order to implement the method or alternate methods. Additionally, individual blocks may be deleted from the method without departing from the spirit and scope of the subject matter described herein. Furthermore, the method can be implemented in any suitable hardware, software, firmware, or combination thereof. However, for ease of explanation, in the embodiments described below, the method may be considered to be implemented in the above-described system and/or the apparatus and/or any electronic device (not shown).

The above description does not provide specific details of manufacture or design of the various components. Those of skill in the art are familiar with such details, and unless departures from those techniques are set out, techniques, known, related art or later developed designs and materials should be employed. Those in the art are capable of choosing suitable manufacturing and design details.

Note that throughout the following discussion, numerous references may be made regarding servers, services, engines, modules, interfaces, portals, platforms, or other systems formed from computing devices. It should be appreciated that the use of such terms is deemed to represent one or more computing devices having at least one processor configured to or programmed to execute software instructions stored on a computer readable tangible, non-transitory medium or also referred to as a processor-readable medium. For example, a server can include one or more computers operating as a web server, database server, or other type of computer server in a manner to fulfill described roles, responsibilities, or functions. Within the context of this document, the disclosed devices or systems are also deemed to comprise computing devices having a processor and a non-transitory memory storing instructions executable by the processor that cause the device to control, manage, or otherwise manipulate the features of the devices or systems.

Some portions of the detailed description herein are presented in terms of algorithms and symbolic representations of operations on data bits performed by conventional computer components, including a central processing unit (CPU), memory storage devices for the CPU, and connected display devices. These algorithmic descriptions and representations are the means used by those skilled in the data processing arts to most effectively convey the substance of their work to others skilled in the art. An algorithm is generally perceived as a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, as apparent from the discussion herein, it is appreciated that throughout the description, discussions utilizing terms such as "generating," or "monitoring," or "displaying," or "tracking," or "identifying," "or receiving," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The methods illustrated throughout the specification, may be implemented in a computer program product that may be executed on a computer. The computer program product may comprise a non-transitory computer-readable recording medium on which a control program is recorded, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other tangible medium from which a computer can read and use.

Alternatively, the method may be implemented in transitory media, such as a transmittable carrier wave in which the control program is embodied as a data signal using transmission media, such as acoustic or light waves, such as those generated during radio wave and infrared data communications, and the like.

The terminology used herein is for the purpose of describing particular embodiments only and is not intended to be limiting of the disclosure. It will be appreciated that several of the above-disclosed and other features and functions, or alternatives thereof, may be combined into other systems or applications. Various presently unforeseen or unanticipated alternatives, modifications, variations, or improvements therein may subsequently be made by those skilled in the art without departing from the scope of the present disclosure as encompassed by the following claim.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A communication system for providing personalized care management comprising:
    a plurality of user devices corresponding to a plurality of authorized caregivers, each user device providing an interactive user interface to:
        provide input data associated with an actionable item being performed for at least one care receiver, wherein the actionable item includes one of: a scheduled actionable item and a non-scheduled actionable item;
    a database for storing profiles of the authorized caregivers and profiles of the at least one care receiver;
    a central controller connected to the plurality of user devices through a communication network to facilitate the authorized caregivers to analyze the profiles of the at least one care receiver from a remote location;
    a hardware processor configured to:
        receive, via the plurality of user devices, the at least one input data based on the scheduled actionable item;
        receive, via the plurality of user devices, the at least one input data based on the non-scheduled actionable item wherein the at least one input data based on the non-scheduled actionable item is inputted into the processing module through at least one Beacon Transmitter or at least one QR Code scanner device;
        update the profile of the at least one care receiver based on the received at least one input data;
        save the updated profile of the at least one care receiver in the database; and
        facilitate the authorized caregivers to further analyze the updated profile of the at least one care receiver.

2. The communication system of claim 1, wherein the profiles of the authorized caregivers are stored in different formats based on specific roles assigned to the authorized caregivers, and location of the plurality of user devices.

3. The communication system of claim 1, wherein the authorized caregivers include at least one of: a family member of the care receiver, an attendant for the care receiver, a nurse for the care receiver, a doctor for the care receiver, or a medicine administrator for the care receiver.

4. The communication system of claim 1, wherein the network is a wired or a wireless network, wherein the wireless network comprising at least one of: a mobile network, a satellite network, a Wi-Fi, or a Wireless Local Area Network (WLAN).

5. The communication system of claim 1, wherein the at least one input data includes a voice input, a text input, a video input, and a touch-based input.

6. The communication system of claim 1, wherein the actionable item includes medical care, psychological care, non-medical care, daily routine care, being provided to the at least one care-receiver by the plurality of authorized caregivers.

7. The communication system of claim 1, wherein the non-scheduled actionable item includes one or more actions which are performed randomly for the care receiver.

8. The communication system of claim 1, wherein the scheduled actionable item includes one or more actions which are performed for the care receiver, according to a schedule prescribed by the corresponding authorized caregivers.

9. A method for providing personalized care/resident management, the method comprising the steps of:
    configuring a plurality of user devices corresponding to a plurality of authorized caregivers, each user device providing an interactive user interface for:
        providing input data associated with an actionable item being performed for at least one care receiver, wherein the actionable item includes one of: a scheduled actionable item and a non-scheduled actionable item;
    configuring a database for storing profiles of the authorized caregivers and profiles of the at least one care receiver;
    configuring a central controller connected to the plurality of user devices through a communication network for facilitating the authorized caregivers to analyze the profiles of the at least one care receiver from a remote location;
    configuring a hardware processor for:
        receiving, via the plurality of user devices, the at least one input data based on the scheduled actionable item;
        receiving, via the plurality of user devices, the at least one input data based on the non-scheduled actionable item wherein the at least one input data based on the non-scheduled actionable item is inputted into the processing module through at least one Beacon Transmitter or at least one QR Code scanner device;
        updating the profile of the at least one care receiver based on the received at least one input data;
        saving the updated profile of the at least one care receiver in the database; and
        facilitating the authorized caregivers to further analyze the updated profile of the at least one care receiver.

10. The method of claim 9, further comprising the step of storing the profiles of the authorized caregivers in different formats based on specific roles assigned to the authorized caregivers, and location of the plurality of user devices.

11. The method of claim 9, wherein the authorized caregivers include at least one of: a family member of the care receiver, an attendant for the care receiver, a nurse for the care receiver, a doctor for the care receiver, or a medicine administrator for the care receiver.

12. The method of claim 9, wherein the at least one input data includes a voice input, a text input, a video input, and a touch-based input.

13. The method of claim 9, wherein the actionable item includes medical care, psychological care, non-medical care, daily routine care, being provided to the at least one care-receiver by the plurality of authorized caregivers.

14. The method of claim 9, wherein the non-scheduled actionable item includes one or more actions which are performed randomly for the care receiver.

15. The method of claim 9, wherein the scheduled actionable item includes one or more actions which are performed for the care receiver, according to a schedule prescribed by the corresponding authorized caregivers.

* * * * *